United States Patent [19]

Cook et al.

[11] Patent Number: 5,204,321
[45] Date of Patent: Apr. 20, 1993

[54] HEPARIN NEUTRALIZATION WITH PLATELET FACTOR 4

[75] Inventors: Jacquelynn J. Cook, Lansdale; Stefan Niewarowski, Narbeth, both of Pa.; Theodore E. Maione, Wakefield, Mass.

[73] Assignee: Repligen Corporation, Cambridge, Mass.

[21] Appl. No.: 902,509

[22] Filed: Jun. 23, 1992

Related U.S. Application Data

[63] Continuation of Ser. No. 480,873, Feb. 16, 1990, abandoned.

[51] Int. Cl.$^5$ .................. A61K 37/02; A61K 31/725; C07K 7/10
[52] U.S. Cl. .................................. 514/2; 514/12; 514/56; 530/380
[58] Field of Search ............... 514/2, 12, 56; 530/380

[56] References Cited

U.S. PATENT DOCUMENTS

| | | | |
|---|---|---|---|
| 3,985,618 | 10/1976 | Innerfield | 435/13 |
| 4,702,908 | 10/1987 | Thorbecke et al. | 514/21 |
| 4,844,895 | 7/1989 | Thorbecke et al. | 514/21 |
| 4,861,757 | 8/1989 | Antoniades et al. | 514/21 |

OTHER PUBLICATIONS

Brindley et al., "Stimulation of Histamine Release from Human Basophils by Human Platelet Factor 4", *J. Clin. Invest.* vol. 72, Oct. 1983, 1218-1223.

Castaneda, "Must Heparin be Neutralized following Open Heart Operations?"*Journal of Thoracic and Cardiovascular Surgery*, vol. 52, No. 5, Nov. 1966, p. 716.

Cavarocchi et al., "Evidence for Complement Activation by Protamine-Heparin Interaction after Cariodpulmonary Bypass", *Surgery*, Sep. 1985, p. 526.

Cella et al., "Human Platelet Factor 4 and Protamine Sulfate Interaction with Glycosaminoglycans in the Rabbit", *European Journal of Clinical Investigation*, 17:548-554 (1987).

Colman, "Humoral Mediators of Catastrophic Reactions Associated with Protamine Neutralization", The Journal of Anesthesiology, vol. 66, No. 5, May 1987, p. 595.

Dawes et al., "The Release, Distribution and Clearance of Human Beta Thromboglobulin and Platelet Factor 4", *Thrombosis Research*, vol. 12, No. 5, pp. 851-861.

Deuel et al., "Platelet Factor 4 is Chemotactic for Neutrophil and Monocytes", *Proc. Natl. Acad. Sci. U.S.A.*, vol. 78, No. 7, pp. 4584-4587, Jul. 1981.

Fehr et al., "In Vivo Complement Activation by Polyanion-Polcation Complexes: Evidence that C5a is Generated Intravascularly During Heparin-Protamine Interaction", *Clinical Immunology and Immunopathology*, 29, 7-14 (1983).

Flicker et al., "Platelet Factor Release following Heparin Administration and during Extracorporeal Circulation", *Trans. Am. Soc. Artif. Intern. Organs*, 1982, p. 431.

Handin et al., "Purification and Binding Properties of Human Platelet Factor 4", The Journal of Biological Chemistry, vol. 251, No. 14, pp. 4273-4282, 1976.

Harker, "Mechanism of Abnormal Bleeding in Patients Undergoing Cardiopulmonary Bypass: Acquired Transient Platelet Dysfunction Associated with Selective Alpha Granule Release", *Blood*, vol. 56, No. 4, Oct. 1980, p. 824.

Hermodson et al., "Isolation, Crystallization and Primary Amino Acid Sequence of Human Platelet Factor 4" (1979) J. Biol. Chem., 252, 6276-6279.

(List continued on next page.)

Primary Examiner—Johnnie R. Brown
Assistant Examiner—Nancy S. Carson
Attorney, Agent, or Firm—Fish & Richardson

[57] ABSTRACT

Circulating heparin in a mammal may be neutralized without substantial depletion of platelets or leukocytes by administering to the mammal a heparin neutralizing amount of purified PF4 or rPF4 or a heparin neutralizing fragment thereof.

19 Claims, 5 Drawing Sheets

OTHER PUBLICATIONS

Holloway et al., "Decreased Platelet Number and Function and Increased Fibrinolysis contribute to Postoperative Bleeding in Cardiopulmonary Bypass Patients", *Thrombosis and Haemostasis*, 59(1) 62–67 (1988).

Holt et al., "Biochemistry of Alpha Granule Proteins", *Sem. in Hemotology*, vol. 22, No. 2, (Arp. 1985), pp. 151–163.

Horrow, "Protamine: A Necessary Evil?" in *Effective Hemostatis in Cardiac Surgery*, Eds. Ellison & Jobes, in press.

Horrow, "Protamine: A Review of its Toxicity", Anest. and Analg. 1985, 64:348–61.

Horrow, "Protamine Allergy" *Journal of Cardiothoracic Anesthesia*, vol. 2, No. 2, (Apr. 1988), pp. 225–242.

Just-Viera et al., "Acute Reaction to Protamine", *The American Surgeon*, Jan. 1984, p. 52.

Lakin et al., "Anaphylaxis to Protamine Sulphate Mediated by Complement Dependent IgG Antibody", *J. of Allergy and Clinical Immunology*, vol. 61, No. 1, Jan. 1978, pp. 102–107.

Lane et al., "Anticoagulant Activities of Heparin Oligosaccharides and their Neutralization by Platelet Factor 4", *Biochem. J.*, (1984) 218, 725–732.

Letters to the *New England Journal of Medicine* concerning Weiss et al., "Life Threatening Reactions to Intravenous Protamine", vol. 321, No. 24, p. 1684, Dec. 1989.

Levine et al., "Human Platelet Factor 4: Purification and Characterization by Affinity Chromatography", *The Journal of Biological Chemistry*, vol. 251 No. 2, pp. 324–328, 1976.

Maione et al., "Inhibition of Angiogenesis by Recombinant Human Platelet Factor 4 and Related Peptides", *Science*, vol. 247, Jan. 5, 1990, p. 77.

Michalski, "Neutralization of Heparin in Plasma by Platelet Factor 4 and Protamine Sulphate", *British Journal of Haematology*, 1978, 38: 561–571.

Morel et al., "Acute Pulmonary Vascoconstriction and Thromboxane Release during Protamine Reversal of Heparin Anticoagulation in Awake Sheep; Evidence for the Role of Reactive Oxygen Metabolytes following Nonimmunological Compliment Activation", *Circulation Research*, vol. 62, No. 5, May 1988, p. 905.

Rao et al., "Effect of Heparin on the In Vivo Release and Clearance of Human Platelet Factor 4", Blood, vol. 61, No. 6, (Jun. 1983), pp. 1208–1214.

Rent et al., "Complement Activation by Interaction of Polyanions and Polycations 1. Heparin-protamine consumptin of Compliment", *The Journal of Immunology*, 1975, p. 120.

Rucinski et al. "Clearance of Human Platelet Factor 4 by Liver and Kidney; It's Alternation by Heparin", *American Journal of Physiology*, Oct. 1986, vol. 251, No. 4, p. H800.

Shanberge et al. "Heparin-Protamine Complexes in the Production of Heparin Rebound and Other Complications of Extra Corporeal Bypass Procedures", *American Journal of Clinical Pathology*, vol. 87, p. 210, 1987.

Shanberge et al., "Interrelationship of Protamine and Platelet Factor 4 in the Neutralization of Heparin", *Thrombosis Research*, 46:89–100, 1987.

Taylor et al., "Comparison of the Cardiovascular Effects of Intravenous and Intra-aortic Protamine in the Conscious and Anesthetized Dog", Ann Thorac Surg, 42:22–26, Jul. 1986.

Walker et al., "Successful Cardiopulmonary Bypass in Diabetics with Anaphylactoid Reactions to Protamine", *British Heart Journal*, 1984, 52:112–4.

Walz et al., "In Vivo Studies on the Binding of Heparin and its Fractions with Platelet Factor 4", *Seminars in Thrombosis and Hemostasis*, vol. 11, No. 1, 1985, p. 40.

Weiss et al., "Association of Protamine IgE and IgG Antibodies with Light Life Threatening Reactions to Intravenous Protamine", *The New England Journal of Medicine*, vol. 320, No. 14, p. 886, 1989.

Cowan et al; Bio Chem. J. 234:485–488 (1986).

Lane et al; J. Biol. Chem. 261(9):3980–3986 (1986).

HEPARIN NEUTRALIZATION WITH PLATELET FACTOR 4

This is a continuation of application Ser. No. 07/480,873, filed Feb. 16, 1990, now abandoned.

FIELD OF THE INVENTION

The invention relates to neutralization of heparin with Platelet Factor- 4 (PF4).

BACKGROUND OF THE INVENTION

Applications of advancing medical technology, such as cardiopulmonary bypass, are associated with a variety of complications. Even in short term use, blood oxygenators produce sufficient activation of clotting pathways to require the use of heparin to inhibit blood coagulation.

An invariable complication of such surgical procedures is a hemorrhagic state manifested by a prolonged bleeding time, causes of which include failure to adequately neutralize heparin and the continuous stimulation of platelets, as manifested by a fall in platelet count, stimulation of thromboxane synthesis and release of platelet granule constituents. (See Colman. *J. Anesthesiology* vol. 66 (5). May. 1987. p. 595). Reversal of heparin is required to restore normal coagulation status and reduce post-operative blood loss.

Protamine is an arginine rich polypeptide (32 amino acids from salmon) commonly used at the conclusion of cardiovascular surgical procedures to neutralize the anticlotting effects of heparin. The use of protamine, however, has been linked to several post-surgical complications, some of which are postoperative systemic hypotension, allergic reactions, catastrophic pulmonary vasoconstriction, acute pulmonary hypertension, complement activation, noncardiogenic pulmonary edema, decreased cardiac output (later event). and thrombocytopenia/leukopenia.

The underlying biochemical basis for these physical complications is poorly understood, but allergic reactions to protamine, have been well documented. Since protamine, usually isolated from fish, can be recognized as a foreign protein by the human immune system, patients with prior protamine exposure are at particular risk during subsequent exposures (Just Viera, J.O., *Amer. Surgeon* 50, (1984), 151–163). Additionally, studies suggest that a non-immunological pathway via complement activation may be responsible for many of the acute reactions observed during protamine reversal of heparin anticoagulation.

To avoid the use of protamine, a number of approaches have been proposed. Construction of bypass circuits with materials that do not activate the coagulation cascade have been suggested, as well as the use of non-heparin anticoagulate preparations. Neutralizing agents for heparin other than protamine are also currently being sought. Horrow, "Effective Hemostasis in Cardiac Surgery", chap. 2, Ellison and Jobes, Eds, in press, 1988. All of these alternatives, presently in various stages of research, have yet to reveal a suitable substitute for protamine that has gained widespread acceptance.

PF4 is a well characterized heparin binding protein found in human plasma at concentrations of 5–20ng/ml. In plasma, in in vitro studies, PF4 has been demonstrated to reverse the effect of heparin on clot formation. Michalski, *Brit. J. Haematol,* 38, 561–571 (1978).

In vivo experiments demonstrate that PF4 is cleared rapidly from circulation in both rats and rabbits. This rapid clearance is due to PF4 binding to endothelial cells. PF4 bound by endothelial cell surfaces can be released into the bloodstream by subsequent administration of heparin. In humans, a similar rise in circulating PF4 concentration is observed following heparin administration.

Platelet concentrate has been shown to have heparin neutralizing activity when administered to humans after bypass surgery, and the effect was attributed to PF4. Walker, *Br. Heart J.* 52:12–14 (1984).

SUMMARY OF THE INVENTION

The invention features a method for the neutralization of heparin in a mammal having an undesirably high level of circulating heparin caused by administration of heparin in connection with a medical procedure such as a surgical or therapeutic procedure, by administering a heparin neutralizing amount of purified PF4 or heparin binding fragments thereof.

Heparin binding fragments are those containing the heparin binding region, amino acids 61 to 66.

The term "purified" as used herein refers to PF4 or recombinant PF4 (rPF4) which is 95% or greater, by weight, PF4 or rPF4, i.e., is substantially free of other proteins, lipids, and carbohydrates with which it is naturally associated.

A purified protein preparation will generally yield a single major band on a polyacrylamide gel for each subunit of PF4 or rPF4. Most preferably, the purified PF4 or rPF4 used in the compositions of the invention is pure as judged by amino terminal amino acid sequence analysis.

We have discovered that normal coagulation status in mammals treated with heparin may be restored after administration of purified PF4 without substantial depletion of platelets or leukocytes or other deleterious effects often associated with the commonly used heparin neutralizing agent, protamine.

In various aspects of the invention: The PF4 or fragment is rPF4 or a fragment thereof. The PF4 or fragment is synthetic PF4 or a fragment thereof. The heparin binding fragment of PF4 contains amino acids 61 to 66. The fragment is C-41. The heparin neutralizing amount is sufficient to neutralize heparin administered at more than 50 units/kg of body weight. The amount is about 0.1 to 20 mg/kg of body weight. The amount is about 6 mg/kg of body weight.

The invention also features a method of restoring a normal coagulation status in a human patient after administration of heparin, without substantial depletion of platelets or leukocytes, by administering purified PF4 or a heparin binding fragment thereof to the patient to form a complex of the heparin with the PF4 or fragment.

The invention also features a method of treating a human patient during a medical procedure, by administering to the patient a therapeutically effective amount of heparin to inhibit coagulation, and thereafter, administering to the patient a therapeutically effective amount of purified PF4 or heparin-binding fragment thereof, to neutralize the heparin.

In various aspects of the invention: The medical procedure involves heart surgery. The medical procedure requires a cardiopulmonary bypass. The medical procedure is an organ transplantation. The medical procedure is a kidney dialysis. The medical procedure is a catheterization. The catheterization is cardiac catheterization. The catheterization is for angioplasty. The medical procedure is for prevention of blood clots formation.

DESCRIPTION OF THE PREFERRED EMBODIMENT

We first briefly describe the drawings.

DRAWINGS

Figure 1:
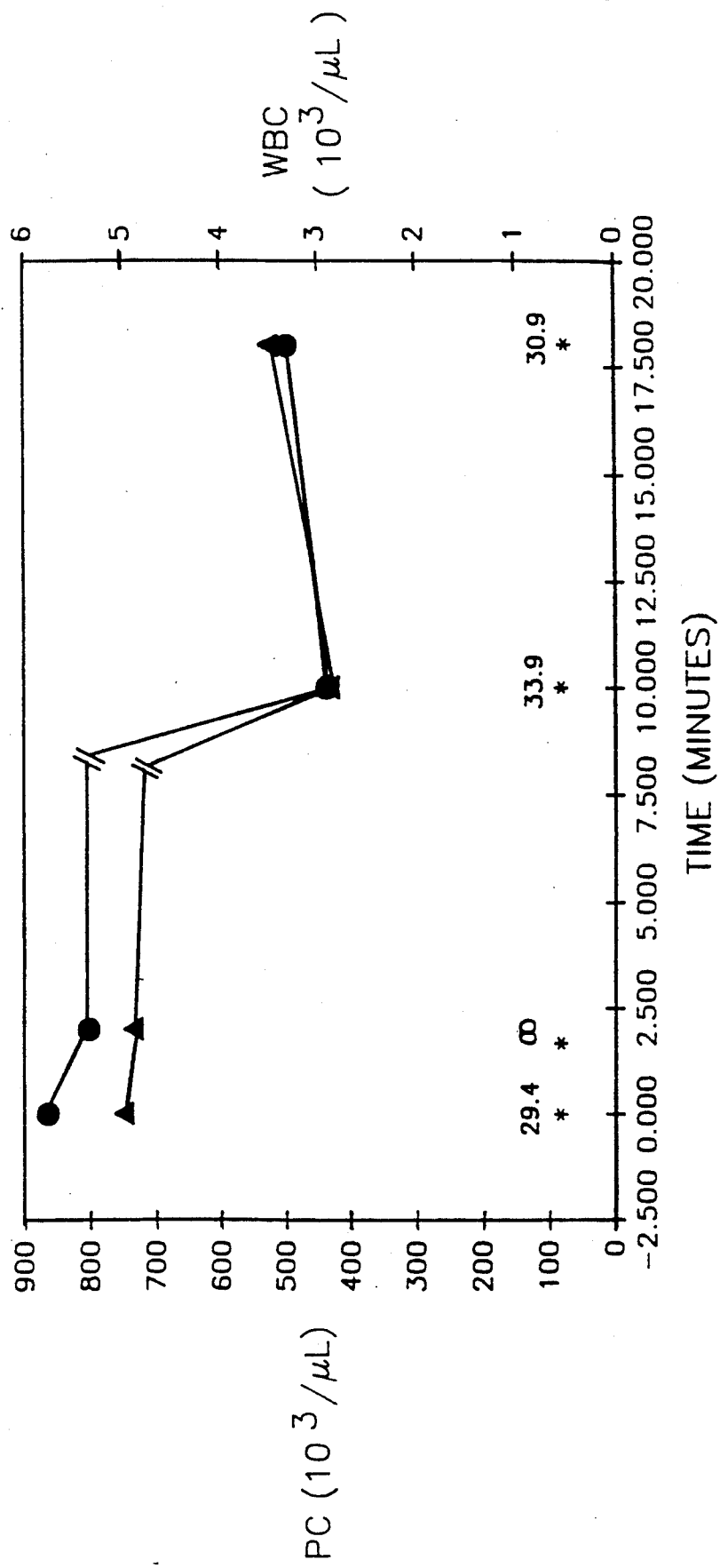
FIG. 1 is a graph showing platelet count, white blood cell count, and activated partial thromboplastin time (APTT) in a rat treated with heparin, as a function of time after injection of protamine sulphate.

As is described in commonly owned U.S. Pat. applications, Ser. No. 295,955, filed Jan. 10, 1989, and U.S. Pat. application Ser. No. 451,021, filed Dec. 27, 1989, the entire contents of both applications being hereby incorporated by reference, human PF4 can be produced by recombinant methods in *E. coli*. A synthetic gene was constructed based on the known PF4 amino acid sequence, and a recombinant fusion protein was expressed which could be purified by heparin-agarose affinity chromatography after chemical cleavage of non-PF4 amino acids from the recombinant fusion protein.

The proteins are cleaved and extracted, and the extracts purified using Heparin-agarose chromatography, removing contaminating proteins with 0.6M NaCl and diluting with 1.2M NaCl. Eluted PF4 is dialyzed into 20 mM acetate buffer, pH 4.0, and then further purified by reverse phase HPLC.

As discussed in the above applications, heparin binding can be attributed to the region of the peptide containing residues 61 to 66. In Vitro Experiments In vitro experiments were conducted to compare the effects of protamine and PF4 for a preliminary assessment of Platelet factor 4 is a well-known protein which has been completely sequenced (Deuel, T. F., R. M. Senior, D. Chang, G. L. Griffin, R. L. Heinrikson, and E. T. Kaiser [1981] Proc. Natl. Acad. Sci. U.S.A. 78:4585-4587). It is a 70-residue secretable platelet protein with a molecular weight of approximately 7.8 Kd which is released during platelet aggregation. Although there is evidence of heparin binding activity and some indications of anti-angiogenesis activity (Folkman, J. [1984] Angiogenesis: Initiation and Modulation, *Cancer Invasion and Metastasis: Biologic and Therapeutic Aspects*, G. L. Nicholson and L. Milas, eds., Raven Press, N.Y., pp, 201-208), PF4 has never been shown to have clinical utility.

rPF4 Production

Recombinant PF4 was produced in *E. coli* as an N-terminal fusion protein containing a unique methionine residue immediately preceding the PF4 portion. More specifically, expression plasmid pPF4-211 was constructed by cloning a synthetic gene encoding native sequence PF4 (see below) (Poncz et al., *Blood*, 69:219 (1987)) into the multiple restriction site region of plasmid pREV2.2 (deposited Jul. 30, 1986; accession #NRRL B-18091). Codon usage in the synthetic gene was optimized for expression in *E. coli*, and synthetic DNA linkers were included on each end to facilitate the directional insertion of the PF4 gene into the vector. The restriction sites HindIII and SmaI were chosen for insertion into pREV2.2. The resulting construct, pPF4-211, expressed a fusion protein containing 34 amino acids of *E. coli* β-glucuronidase (BG) separated from the PF4 sequence by a unique methionine residue.

DNA and Amino Acid Sequence of Native rPF4

```
GAT CAA GCT TCT ATG GAA GCT GAA GAA GAC
    TT CGA AGA TAC CTT CGA CTT CTT CTG
              Met Glu Ala Glu Glu Asp

GGT GAC CTG CAG TGC CTG TGC GTT AAA ACT
CCA CTG GAC GTC ACG GAC ACG CAA TTT TGA
Gly Asp Leu Gln Cys Leu Cys Val Lys Thr

ACT TCT CAG GTT CGG CCG CGT CAT ATC ACT
TGA AGA GTC CAA GCC GGC GCA GTA TAG TGA
Thr Ser Gln Val Arg Pro Arg His Ile Thr

AGT CTG GAA GTT ATC AAA GCT GGT CCG CAT
TCA GAC CTT CAA TAG TTT CGA CCA GGC GTA
Ser Leu Glu Val Ile Lys Ala Gly Pro His

TGC CCG ACT GCT CAG CTG ATC GCT ACT CTG
ACG GGC TGA CGA GTC GAC TAG CGA TGA GAC
Cys Pro Thr Ala Gln Leu Ile Ala Thr Leu

AAA AAC GGT CGT AAA ATC TGC CTG GAC CTG
TTT TTG CCA GCA TTT TAG ACG GAC CTG GAC
Lys Asn Gly Arg Lys Ile Cys Leu Asp Leu

CAG GCG CCG CTG TAC AAA AAA ATC ATC AAA
GTC CGC GGC GAC ATG TTT TTT TAG TAG TTT
Gln Ala Pro Leu Tyr Lys Lys Ile Ile Lys

AAA CTG CTG GAA TCC TGA TCC GGT ACC CGG
TTT GAC GAC CTT AGG ACT AGG CCA TGG GCC
Lys Leu Leu Glu Ser

GAG CTC
C
```

Cells expressing the fusion protein were subjected to lysozyme (1 mg/g cells), DNase I (500 units/100 g cells) and bead mill treatments. The lysis pellet containing the fusion protein was treated with CNBr (10 g/100 g cells) in 70% formic acid to cleave the fusion protein at the methionine between the BG and PF4 portions. Following evaporation of the CNBr/formic acid, the recombinant protein was extracted with 200 ml of 50 mM Tris-Cl, pH 7.6, 5 mM EDTA, and 10 mM DTT per 100 g of cell starting material. Native sequence rPF4-211 was purified by binding the protein to heparin agarose, removing contaminating proteins with 0.6M NaCl, and eluting with 1.2M NaCl. The resulting material was dialyzed into 20 mM sodium acetate, pH 4.0, and analyzed on a 15% SDS-PA gel stained with Coomassie Brilliant Blue. Minor contaminants could be removed using C4 reverse phase high pressure liquid chromatography (HPLC) to prepare the protein for in vivo use.

PF4 peptides

Peptides were prepared by standard solid phase synthesis procedures, cleaved from the solid support and deblocked, and purified by reverse phase HPLC.

Heparin Binding Fragments

The lysine rich region of PF4 (residues 61–66) is also the domain associated with the binding of heparin by PF4. Heparin is known to play a role in modulating angiogenesis, which can also be affected by protamine, another well characterized heparin-binding protein. To assess the ability of PF4-based synthetic peptides to bind heparin, we assayed the activity of coagulation-cascade enzymes which are inhibited by heparin. The Factor Xa assay used here has previously been described in Denton et al., *Biochem. J.*, 209:455–460 (1983). Protamine and platelet factor 4 are able to prevent the heparin inhibition of thrombin and Factor Xa at approximately equimolar concentrations. The 41 amino acid C-terminal peptide of PF4 (C-41) prevented heparin inhibition less effectively, but the C-13 peptide was unable to prevent the inhibition of thrombin even at concentrations ten times that of an effective level of rPF4.

The proteins are cleaved and extracted, and the extracts purified using Heparin-agarose chromatography, removing contaminating proteins with 0.6M NaCl and diluting with 1.2M NaCl. Eluted PF4 is dialyzed into 20 mM acetate buffer, pH 4.0, and then further purified by reverse phase HPLC.

As discussed in the above applications, heparin binding can be attributed to the region of the peptide containing residues 61 to 66.

In Vitro Experiments

In vitro experiments were conducted to compare the effects of protamine and PF4 for a preliminary assessment of whether PF4 might be a suitable substitute. Additionally, human platelet-derived PF4 and rPF4 were compared.

In all properties examined, human PF4 and rPF4 showed essentially identical characteristics. PF4 isolated from platelets and recombinant *E. coli* cells were compared for their abilities to prevent heparin inhibition of Factor Xa (essential for the production of thrombin) in vitro. The two protein preparations showed identical capacity for neutralization of heparin, with 1 nmol of protein neutralizing approximately 0.25nmol (0.1 unit) heparin in this assay.

The abilities of protamine and rPF4 to prevent heparin-inhibition of the coagulation enzyme Factor Xa were compared. The details of the assay are described by Denton et al, 1983, *Biochem. J.* 209:455. In the Factor Xa assay, 0.5 units of heparin inhibited enzymatic activity almost 90%. At low concentrations, both rPF4 and protamine partially restored Factor Xa activity, but at concentrations greater than 1 $\mu$M, rPF4 was clearly more effective in preventing Factor Xa inhibition.

In experiments carried out under conditions similar to the Factor Xa experiments, thrombin was inhibited 99% by 0.25 units of heparin. Both rPF4 and protamine completely prevented heparin inhibition at 1 $\mu$M and showed no significant difference in their molar dose responses.

Neutralization of heparin in human plasma was also examined. The activated partial thromboplastin time (APTT) of normal human plasma was increased from its base level of approximately 30 seconds to 195 seconds by the addition of 1 unit/ml of heparin. When added during the incubation preceding the addition of the activated thromboplastin, rPF4 and protamine were equally effective in restoring the APTT to its heparin-free level.

Similar studies and results may be obtained using certain fragments of PF4 or rPF4 that include the heparin binding region, residues 61–66. For example, C-41, a 41 amino acid C-terminal peptide of PF4 described in U.S. Pat. application Ser. No. 295,555, (now abandoned) incorporated above, demonstrated the ability to neutralize heparin in vitro using the Factor Xa assay.

In Vivo Experiments

In Vivo experiments were performed on rats to compare the heparin neutralizing activity of protamine and PF4 and to investigate the effect of PF4 on platelet and white blood cell count.

Sprague Dawley rats (225g) were anesthetized with pentobarbital, the trachea was intubated, and the right femoral vein and carotid artery were cannulated. The intravenous infusion of heparin was followed by infusion of either protamine or rPF4. Arterial blood samples were taken prior to and immediately after heparin infusion and at several time points following the infusion of the neutralizing agent. Controls were conducted with Ringer s solution in place of heparin and the experimental agents. Samples were used for the following determinations: clotting time, platelet count, and white blood cell count.

Figure 2:
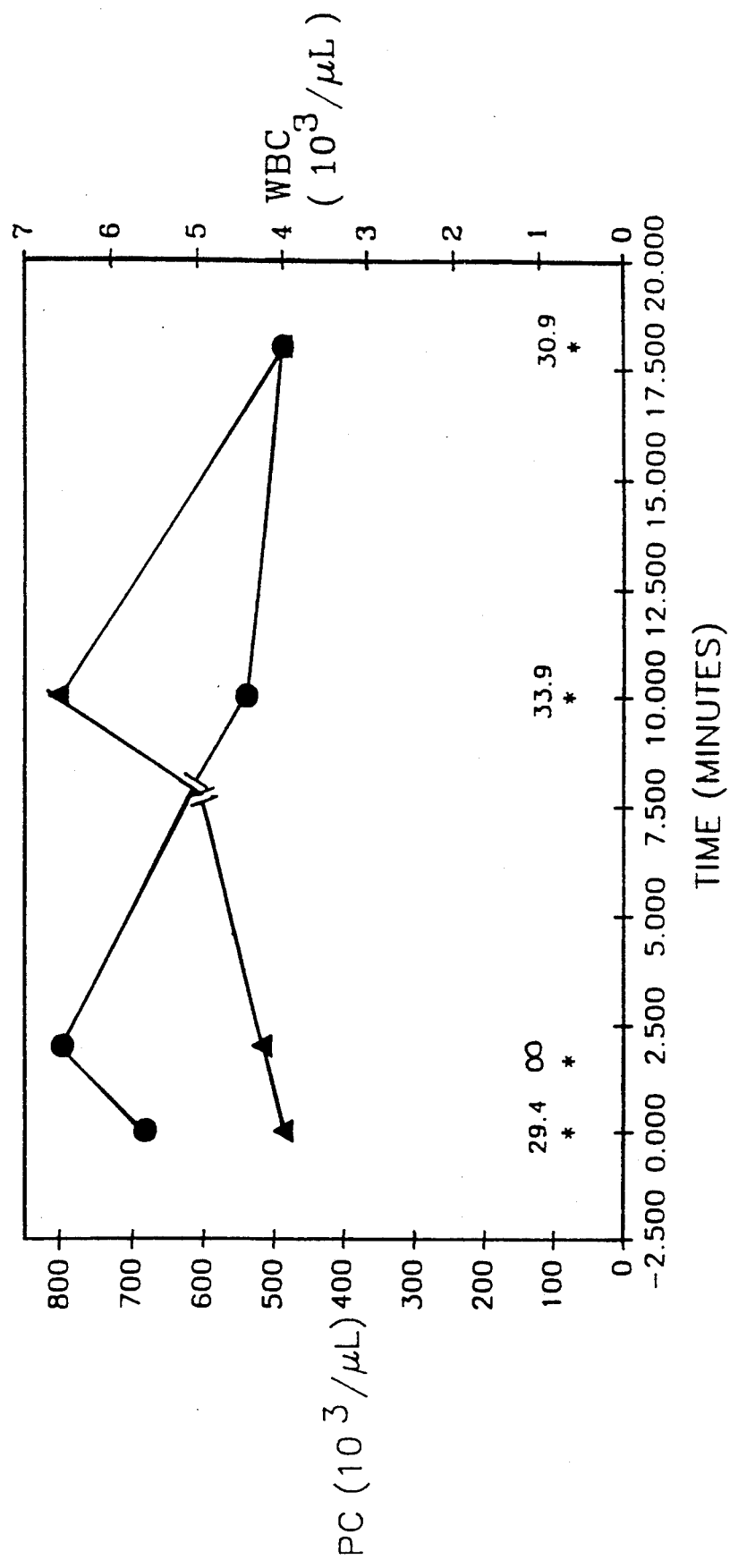
FIG. 2 is a graph showing platelet count, white blood cell count, and APTT in a rat treated with heparin as a function of time after injection of rPF4.

Referring to FIGS. 1 and 2, data are shown from a typical experiment comparing the platelet count, white blood cell count and the APTT in rats when injected with heparin followed by protamine sulfate (FIG. 1) and when injected with heparin followed by rPF4 (FIG. 2). In these FIGS., heparin was injected at t=0 and either protamine sulfate or rPF4 injected two minutes thereafter (t=2 minutes). The dosages used were: heparin 1 unit/g animal wt.; protamine sulfate 1 ug/g animal wt.; and PF4 7.5 ug/g animal wt.

In FIG. 1, the effect of protamine is shown to produce a decrease in the APTT to approximately normal levels after about 10 minutes. There was also observed a significant decrease of white blood cell count and platelet count after injection with protamine sulfate. Ten minutes after injection of heparin and eight minutes after injection of protamine sulfate, platelet count had fallen from over $800 \times 10^3/\mu l$ (measured at t=0) to less than $500 \times 10^3/\mu l$ (measured at t=10 minutes). Similarly, white blood count fell from over $5 \times 10^3/\mu l$ (t=0) to less than about $3 \times 10^3/\mu l$ (t=10 minutes). These rats also had respiratory problems.

Administration of rPF4 also effectively neutralized heparin, as shown by restoration of normal APTT levels at t=10 minutes (ten minutes after injection of heparin and eight minutes after injection of rPF4; FIG. 2). Neutralization of heparin by rPF4 did not lead to the extensive depletion of platelet and white blood cells as caused by protamine sulfate. Platelet count remained relatively stable falling only from the initial value of $700 \times 10^3/\mu l$ (t=0) to about $500 \times 10^3/\mu l$ (t=10 minutes). White blood cell count remained relatively stable at about $4 \times 10^3/\mu l$ throughout the tests.

Experiments were also conducted to investigate hematocrit levels under conditions as described with respect to FIGS. 1 and 2. No change in hematocrit levels were observed when either PF4 or protamine were used for heparin neutralization.

In addition, three experiments were performed in which heparinized rats were injected with low doses of rPF4 (150 $\mu$g/100g). In these rats the anticoagulant effect of heparin was partially neutralized and no effect on platelets and white blood cells was observed.

Figure 3:
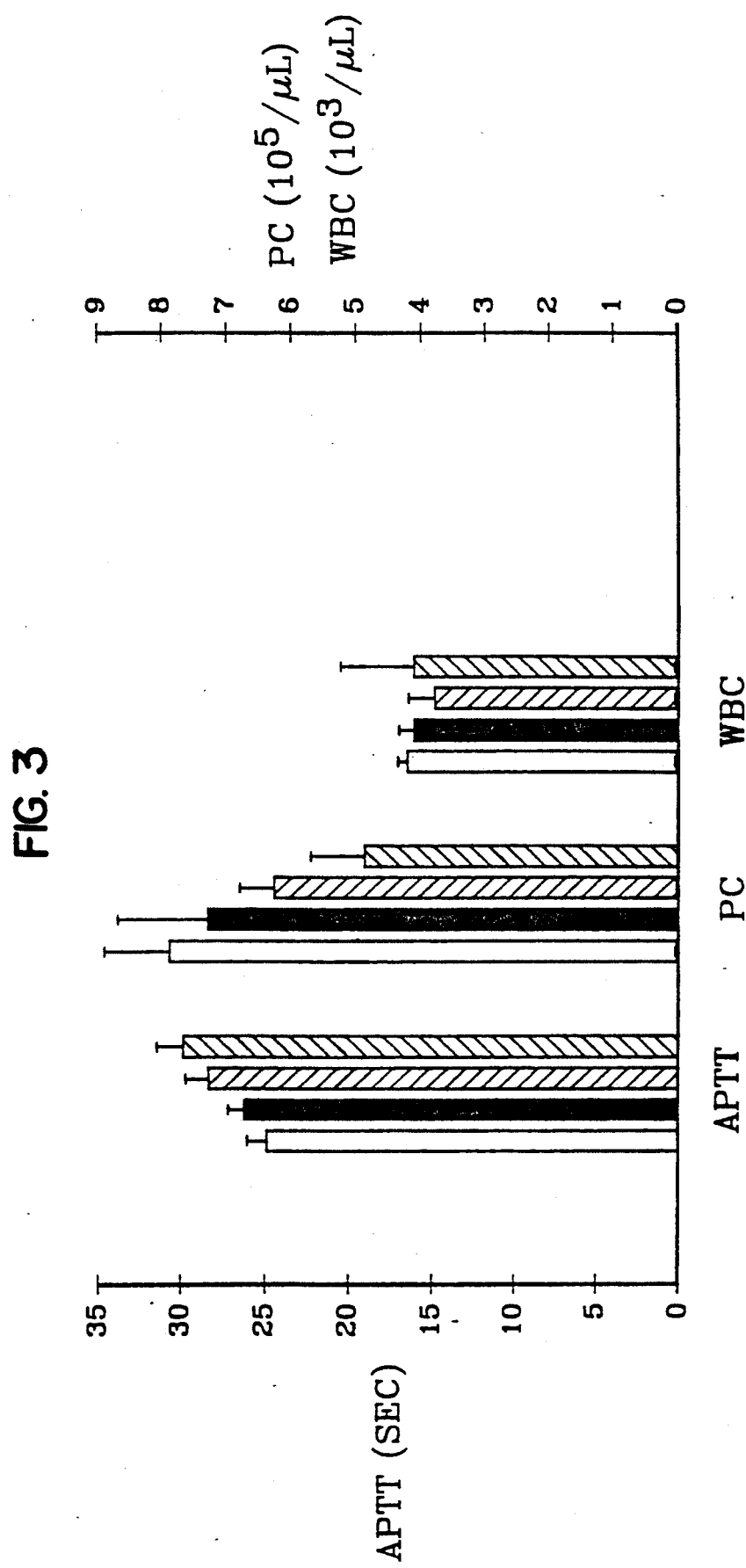
FIGS. 3 to 5 are bar graphs illustrating variations in white blood cell count, platelet count, and APTT of rats treated with heparin, after administration of a control solution (FIG. 3), protamine sulfate (FIG. 4), and rPF4 (FIG. 5). PF4
Figure 4:
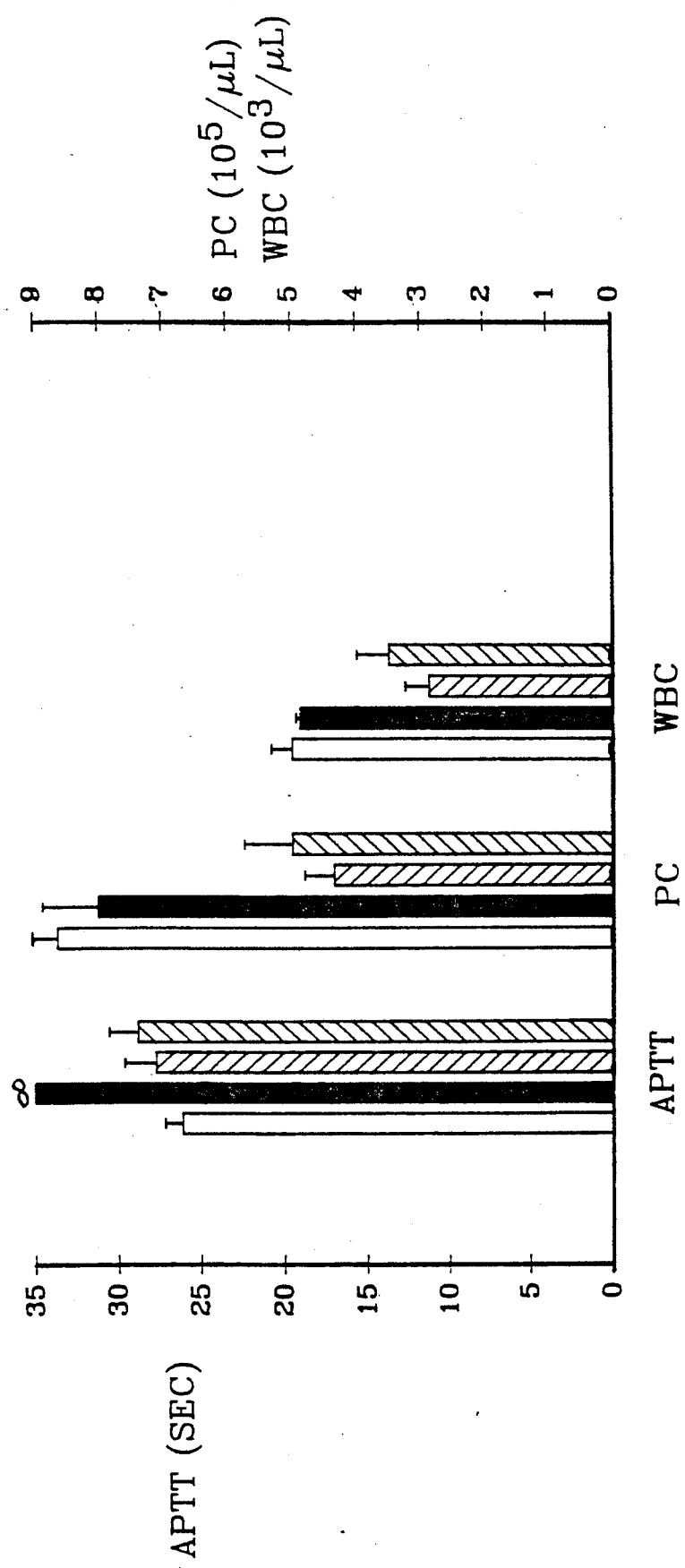
Figure 5:
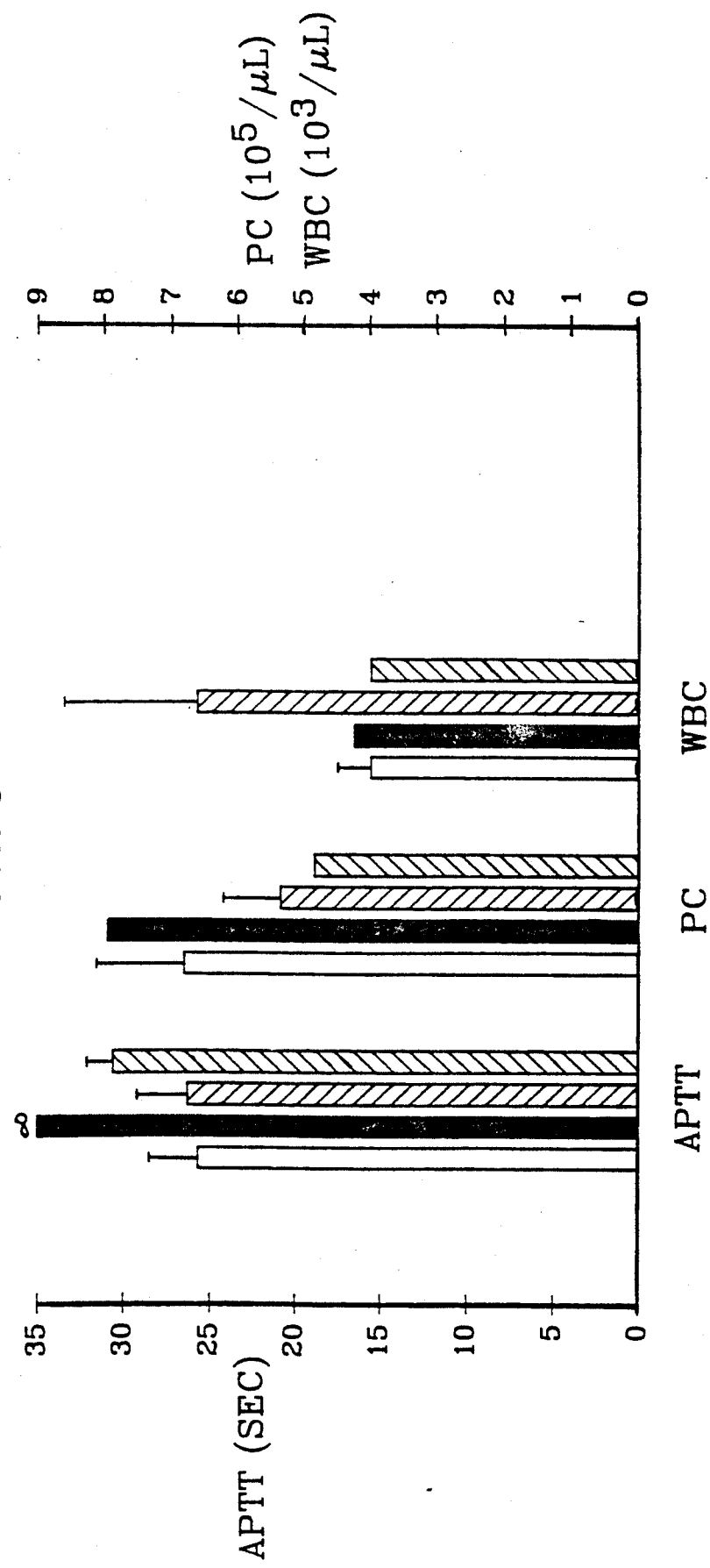

Referring now to FIGS. 3 to 5, statistical bar graph data are shown comparing APTT, platelet count, (PC) and white blood cell (WBC) count in rats injected with a control solution, Ringers solution (FIG. 3), injected with heparin followed by protamine sulfate (FIG. 4) and injected with heparin followed by rPF4 (FIG. 5). The data included control rats, five rats injected with heparin followed by protamine sulfate and two rats injected with heparin followed by rPF4.

FIG. 3 shows APTT, PC and WBC in rats after injection of mammalian Ringer's solution. Samples A were taken before injection; samples B, 2 min after injection; samples C, 10 min after injection; and samples D, 18 min after injection. Data represents mean values and S.E.M. from 5 experiments.

FIG. 4 shows APTT, PC and WBC in rats after injection of heparin (100 units/100g) followed by protamine sulfate (100µg/100g). Samples A were taken before injection; samples B, 2 min after heparin injection; samples C, 10 min after heparin and 8 min after protamine sulfate injection; and samples D, 18 min after heparin injection. Data represent mean values and S.E.M. from experiments except that white blood cells and platelets were counted only in 3 samples taken at 2 and at 18 min after heparin injection. The data in FIG. 4 indicate a drop in platelet and white blood cell counts in samples after protamine sulfate injection to heparinized rats. The decrease was statistically significant ($p < 0.01$) as compared to samples obtained before heparin injection.

FIG. 5 shows APTT, PC, and WBC in rats after injection of heparin followed by rPF4 (7.5 µg/g). Data represent mean values and S.E.M. from 2 experiments for samples taken at times A–D as indicated in the discussion above with respect to FIG. 4. The injection of rPF4 did not produce a statistical decrease in platelet and white blood count.

As evident in the comparison of FIGS. 3, 4 and 5, platelet count remains relatively constant when rPF4 is administered to neutralize heparin (FIG. 5) compared to when protamine is administered to neutralize heparin (FIG. 4). Statistically, platelet count decreased significantly in the presence of protamine (48±12.2% of initial) but remains normal following rPF4 (89±4.9%). WBC count also decreased following protamine sulfate treatment. These results indicate that PF4 is superior to protamine in heparin neutralization in a number of respects.

USE

Purified rPF4 is prepared by a rigorously controlled procedure and substantially free of contaminants.

PF4 can be administered intravenously following heparin treatment, for example, using a slow drip i.v. infusion over the course of 10 minutes. PF4 may be employed following heparin treatment in any surgical procedure in which heparin is employed or therapeutically when heparin is used to avoid clotting. A typical effective dose of rPF4 is approximately 6.35 mg per kg of body weight, based on an effective protamine dose of approximately 3.6 mg per kg of body weight. However, the actual dosage may vary with the dosage of heparin.

Other embodiments are within the following claims.

We claim:

1. A method for completely preventing heparin inhibition of coagulation in a mammal having an undesirably high level of circulating heparin following administration of heparin in connection with a medical procedure, said method comprising administering to said mammal a heparin neutralizing amount of purified PF4 or purified recombinant PF4.

2. The method of claim 1 wherein said PF4 is recombinant PF4.

3. The method of claim 1 wherein said PF4 is synthetic PF4.

4. The method of claim 1 wherein said PF4 comprises a heparin binding fragment, said fragment comprising the heparin binding region of said PF4 corresponding to amino acids 61 to 66.

5. The method of claim 4 wherein said fragment is C-41.

6. The method of claim 1 wherein said amount is sufficient to completely prevent heparin inhibition of coagulation when said heparin is administered at more than 50 units/kg of body weight of the mammal.

7. The method of claim 1 wherein said amount is about 6.0 to 20 mg/kg of body weight of the mammal.

8. The method of claim 7 wherein said amount is about 6 mg/kg of body weight.

9. A method of restoring a normal coagulation status in a human patient after administration of heparin, without substantial depletion of platelets or leukocytes, comprising administering purified PF4 or purified recombinant PF4 to said patient to form a complex of said heparin with said PF4.

10. A method of treating a human patient to temporarily prevent blood coagulation during a medical procedure, comprising:
   administering to said patient a therapeutically effective amount of heparin to inhibit coagulation, and thereafter
   administering to said patient a therapeutically effective amount of purified PF4 or purified recombinant PF4 to neutralize said heparin.

11. The method of claim 10 wherein said medical procedure is heart surgery.

12. The method of claim 10 wherein said medical procedure is a cardiopulmonary bypass.

13. The method of claim 10 wherein said medical procedure is an organ transplantation.

14. The method of claim 10 wherein said medical procedure is a kidney dialysis.

15. The method of claim 10 wherein said medical procedure is a catheterization.

16. The method of claim 15 wherein said catheterization is cardiac catheterization.

17. The method of claim 15 wherein said catheterization is diagnostic.

18. The method of claim 15 wherein said catheterization is for angioplasty.

19. The method of claim 10 wherein said medical procedure is for prevention of blood clot formation.

* * * * *

UNITED STATES PATENT AND TRADEMARK OFFICE
CERTIFICATE OF CORRECTION

PATENT NO. : 5,204,321
DATED : April 20, 1993
INVENTOR(S) : Jacquelynn J. Cook, et al It is certified that error appears in the above-indentified patent and that said Letters Patent is hereby corrected as shown below:

Column 3, line 23, after "Ser. No. 295,955", add —now abandoned—;
       lines 34-45 should be deleted;
Column 6, lines 2, change "Ser. No. 295,555" to —Ser. No. 295,955—

Signed and Sealed this

Twenty-ninth Day of March, 1994

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO.  : 5,204,321
DATED       : April 20, 1993
INVENTOR(S) : Jacquelynn J. Cook, et. al.

It is certified that error appears in the above-indentified patent and that said Letters Patent is hereby corrected as shown below:

Claim 4, column 8, line 14, delete "fragment", both occurrences, and insert therefore -- domain --.

Claim 5, column 8, lines 17-18, delete "The method of claim 4 wherein said fragment is C-41." and insert therefor --The method of claim 1, wherein said PF4 comprises heparin binding fragment C-41.--

Signed and Sealed this

Twenty-fourth Day of October, 1995

Attest:

BRUCE LEHMAN

Attesting Officer          Commissioner of Patents and Trademarks